(12) United States Patent
Schweinfurth et al.

(10) Patent No.: US 11,755,703 B2
(45) Date of Patent: Sep. 12, 2023

(54) VOICE AUTHENTICATION SYSTEMS AND METHODS FOR PRESCRIPTION PROCESSES

(71) Applicant: WALGREEN CO., Deerfield, IL (US)

(72) Inventors: Andrew Schweinfurth, Chicago, IL (US); Julija Alegra Petkus, Oak Park, IL (US); Gunjan Dhanesh Bhow, Menlo Park, CA (US)

(73) Assignee: WALGREEN CO., Deerfield, IL (US)

( * ) Notice: Subject to any disclaimer, the term of this patent is extended or adjusted under 35 U.S.C. 154(b) by 587 days.

(21) Appl. No.: 16/807,999

(22) Filed: Mar. 3, 2020

(65) Prior Publication Data

US 2022/0391479 A1    Dec. 8, 2022

Related U.S. Application Data

(60) Provisional application No. 62/902,110, filed on Sep. 18, 2019.

(51) Int. Cl.

| | |
|---|---|
| *G06F 21/00* | (2013.01) |
| *G06F 21/32* | (2013.01) |
| *G16H 10/60* | (2018.01) |
| *G16H 40/20* | (2018.01) |
| *G10L 17/06* | (2013.01) |
| *G10L 25/51* | (2013.01) |

(Continued)

(52) U.S. Cl.
CPC ............ *G06F 21/32* (2013.01); *G06F 3/0481* (2013.01); *G06F 3/167* (2013.01); *G06F 21/6245* (2013.01); *G06Q 50/265* (2013.01); *G10L 15/22* (2013.01); *G10L 17/00* (2013.01); *G10L 17/06* (2013.01); *G10L 17/22* (2013.01); *G10L 25/51* (2013.01); *G16H 10/60* (2018.01); *G16H 20/10* (2018.01); *G16H 40/20* (2018.01); *G16H 40/63* (2018.01); *G16H 80/00* (2018.01); *G10L 2015/223* (2013.01); *G10L 2015/228* (2013.01)

(58) Field of Classification Search
CPC ......... G06F 21/32; G10L 17/00; G16H 10/60; G16H 20/10
See application file for complete search history.

(56) References Cited

U.S. PATENT DOCUMENTS

| | | | |
|---|---|---|---|
| 7,853,241 B1 | 12/2010 | Harrison | |
| 8,095,381 B2 * | 1/2012 | Simons | G16H 10/60 600/300 |

(Continued)

OTHER PUBLICATIONS

European Patent Application No. 20195204.1, Extended European Search Report, dated Feb. 11, 2021.

(Continued)

*Primary Examiner* — Jeffrey C Pwu
*Assistant Examiner* — William A Corum, Jr.
(74) *Attorney, Agent, or Firm* — MARSHALL, GERSTEIN & BORUN LLP; Randall G. Rueth

(57) ABSTRACT

Methods and systems may incorporate voice interaction and other audio interaction to facilitate access to prescription related information and processes. Particularly, voice/audio interactions may be utilized to achieve authentication to access prescription-related information and action capabilities. Additionally, voice/audio interactions may be utilized in performance of processes such as obtaining prescription refills and receiving reminders to consume prescription products.

12 Claims, 10 Drawing Sheets

(51) Int. Cl.
*G06Q 50/26* (2012.01)
*G16H 20/10* (2018.01)
*G16H 40/63* (2018.01)
*G10L 15/22* (2006.01)
*G06F 3/16* (2006.01)
*G16H 80/00* (2018.01)
*G06F 3/0481* (2022.01)
*G10L 17/22* (2013.01)
*G10L 17/00* (2013.01)
*G06F 21/62* (2013.01)

(56) References Cited

U.S. PATENT DOCUMENTS

| | | |
|---|---|---|
| 8,588,765 B1 | 11/2013 | Harrison |
| 10,057,227 B1 | 8/2018 | Hess et al. |
| 2008/0141353 A1 | 6/2008 | Brown |
| 2013/0060569 A1 | 3/2013 | Fu et al. |
| 2014/0142971 A1* | 5/2014 | Panagakos ............ G06Q 10/10 705/2 |
| 2014/0284348 A1 | 9/2014 | Cheng |
| 2016/0378949 A1 | 12/2016 | Fu et al. |
| 2017/0213001 A1 | 7/2017 | Harrison |
| 2017/0220762 A1 | 8/2017 | Toupin et al. |
| 2018/0068103 A1 | 3/2018 | Pitkanen et al. |
| 2019/0114685 A1 | 4/2019 | Postrel |
| 2019/0228850 A1 | 7/2019 | Ramaci |
| 2019/0267123 A1 | 8/2019 | Stueckemann et al. |
| 2019/0279647 A1 | 9/2019 | Jones et al. |
| 2019/0362064 A1 | 11/2019 | Zhang et al. |
| 2021/0081517 A1* | 3/2021 | Atkinson ............... G06V 40/50 |
| 2021/0287794 A1 | 9/2021 | Alden et al. |
| 2021/0319872 A1* | 10/2021 | Valentine ............... G16H 10/60 |
| 2021/0398633 A1 | 12/2021 | Baum et al. |

OTHER PUBLICATIONS

European Application No. 20195206, Extended European Search Report, dated Feb. 11, 2021.
European Patent Application No. 20195196.9, Extended European Search Report, dated Feb. 15, 2021.
European Patent Application No. 20195199.3, Extended European Search Report, dated Feb. 15, 2021.
European Patent Application No. 2019/5210.8, Extended European Search Report, dated Feb. 16, 2021.

* cited by examiner

VOICE AUTHENTICATION SYSTEMS AND METHODS FOR PRESCRIPTION PROCESSES

FIELD OF DISCLOSURE

The present disclosure generally relates to use of voice interaction and other audio interaction to facilitate access to prescription-related information and processes.

BACKGROUND

Reliability and ubiquity of voice recognition technology has increased in recent years. Various electronic devices, including but not limited to smartphones, tablets, laptop computers, smart wearable devices, and dedicated speakers, are capable of both producing and receiving sound including speech. Moreover, these electronic devices are increasingly interconnected via WiFi, Bluetooth, and other communications over the Internet.

In the field of electronic prescription management, websites and applications have been developed to facilitate processes such as viewing information related to a medical prescription, ordering fills or refills of prescription products, and providing reminders to consume prescription products. However, providing an individual with access to certain protected health information (PHI) often requires high levels of assurance of the individual's identity.

SUMMARY

At a high level, methods and systems described herein incorporate voice interactions and other audio interactions to facilitate access to prescription-related information and processes.

In one embodiment, a computer-implemented method is provided for authenticating a user to access a prescription resource. The method may include (1) obtaining, via one or more processors, an indication of a request to access the prescription resource, the request obtained via an electronic computing device associated with a user, (2) identifying, via the one or more processors, an authentication action prerequisite to providing access to the requested prescription resource, (3) obtaining, via the one or more processors, voice data corresponding to the user, the voice data provided by the user via a microphone of the electronic computing device, (4) comparing, via the one or more processors, the obtained voice data to reference voice data corresponding to one or more persons authorized to access the requested prescription resource, (5) based at least in part upon the comparison, authenticating, via the one or more processors, the user to access the requested prescription resource, and/or (6) providing, via the one or more processors, one or more user interfaces to the electronic computing device to facilitate access to the requested prescription resource. The method may include additional, fewer, and/or alternate actions, including actions described herein.

In another embodiment, a computing system is provided for authenticating a user to access a prescription resource. The computing system may include one or more processors and one or more memories storing non-transitory computer executable instructions. The instructions, when executed by the one or more processors, may cause the computing system to (1) obtain an indication of a request to access the prescription resource, the request obtained via an electronic computing device associated with a user, (2) identify an authentication action prerequisite to providing access to the requested prescription resource, (3) obtain voice data corresponding to the user, the voice data provided by the user via a microphone of the electronic computing device, (4) compare the obtained voice data to reference voice data corresponding to one or more persons authorized to access the requested prescription resource, (5) based at least in part upon the comparison, authenticate the user to access the requested prescription resource, and/or (6) provide one or more user interfaces to the electronic computing device to facilitate access to the requested prescription resource. The computing system may include additional, fewer, and/or alternate components, and may be configured to perform additional, fewer, and/or alternate actions, including those described herein.

In yet another embodiment, one or more non-transitory computer readable media are provided. The one or more non-transitory computer readable media may store computer executable instructions. The instructions, when executed by one or more processors, may cause the one or more processors to (1) obtain an indication of a request to access a prescription resource, the request obtained via an electronic computing device associated with a user, (2) identify an authentication action prerequisite to providing access to the requested prescription resource, (3) obtain voice data corresponding to the user, the voice data provided by the user via a microphone of the electronic computing device, (4) compare the obtained voice data to reference voice data corresponding to one or more persons authorized to access the requested prescription resource, (5) based at least in part upon the comparison, authenticate the user to access the requested prescription resource, and/or (6) provide one or more user interfaces to the electronic computing device to facilitate access to the requested prescription resource. The one or more non-transitory computer readable media may include additional, fewer, and/or alternate instructions, including those described herein.

BRIEF DESCRIPTION OF THE DRAWINGS

The figures described below depict various aspects of the systems and methods disclosed herein. Advantages will become more apparent to those skilled in the art from the following description of the preferred embodiments which have been shown and described by way of illustration. The present embodiments may be capable of other and different embodiments, and their details are capable of modification in various respects. Accordingly, the drawings and description are to be regarded as illustrative in nature and not as restrictive. Further, wherever possible, the following description refers to the reference numerals included in the following figures, in which features depicted in multiple figures are designated with consistent reference numerals.

DETAILED DESCRIPTION

The present disclosure generally relates to the use of voice interactions and other audio interactions to facilitate access to prescription-related information and processes.

As described herein, the term "prescription" generally refers to a medical prescription issued by a medical professional, the prescription authorizing a patient to obtain, use, and/or consume one or more "prescription products." A prescription product, as described herein, may include an orally consumable product (e.g., a blood pressure medication pill), an intravenous product, a medical device, and/or other products to which a prescription may pertain.

Accordingly, "prescription-related information," as described herein, may generally include information pertaining to (1) the prescribed product(s), (2) the patient and/or another person authorized to receive and/or handle the prescribed product(s), (3) a medical professional and/or pharmacy via which the product(s) are obtained, and/or other suitable information, including information described herein. "Prescription-related actions" (or "tasks," "processes," etc.), may include, for example, actions related to (1) viewing prescription-related information, (2) obtaining or refilling a prescription product, (3) consuming a prescription product, and/or other actions described herein. A "prescription resource," as described herein, may refer collectively to prescription-related information and/or prescription-related action capabilities to which a user of systems/methods herein seeks access. A "user," as described herein, may refer to a patient having the prescription, and/or to a caregiver, parent, guardian, pharmacist, doctor, and/or other individual having access to prescription resources on behalf of the patient.

I. Example Computing Environment

Figure 1:
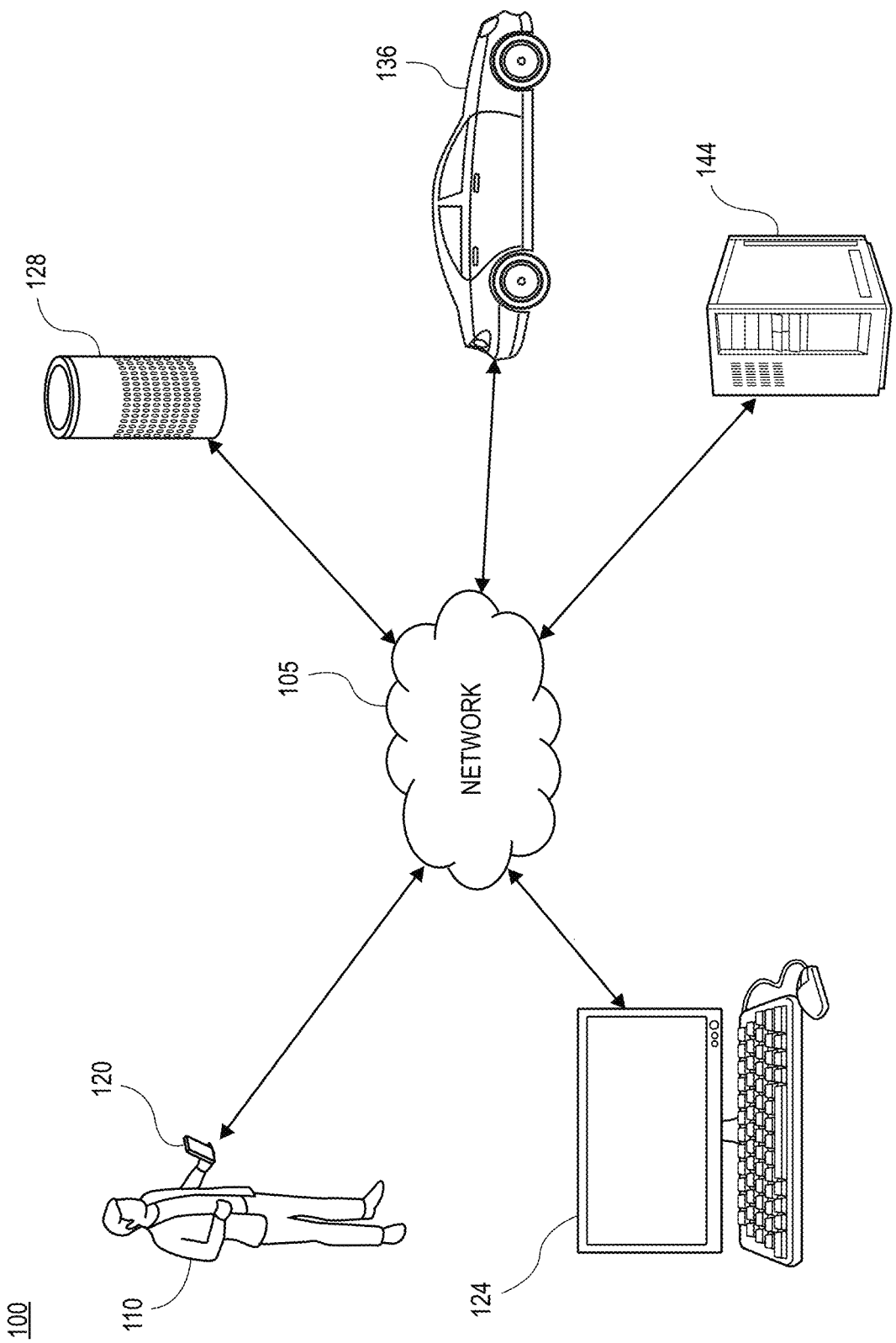
FIG. 1 depicts an example computing environment comprising various computing elements via which techniques described herein may be implemented, in accordance with some embodiments.

FIG. 1 depicts an example computing environment 100 comprising various computing elements via which techniques described herein may be implemented, in accordance with some embodiments.

In various embodiments, elements of the computing environment 100 may establish communicative connections and exchange information via one or computing networks 105 (simply, "network 105"). The network 105 may, for example, include networks such as the Internet, PTSN, a local area network (LAN), and/or a wireless LAN (WLAN). In some embodiments, communications via the network 105 may comprise communications via Bluetooth or other short-range communication standards.

Devices included in the environment 100 may generally receive, transmit, and/or display prescription-related information, and/or perform prescription-related actions, on behalf of a user 110. The user 110 may, for example, be a patient to whom a prescription pertains. Additionally or alternatively, the user 110 may be a caregiver, parent, or other person associated with the patient and who may be authorized to access prescription resources on behalf of the patient. Computing elements of the environment 100 may display information on behalf of the user 110 via various visual interfaces (e.g., graphical user interfaces), examples of which will be provided herein. Furthermore, as will be described herein, elements of the computing environment 100 may receive and detect audio including speech signals from the user 110.

More particularly, the example computing environment 100 may include one or more personal electronic devices ("personal devices") 120. A personal device may be, for example, a smartphone, a tablet computing device, a smart wearable computing device, and/or another computing device. Each personal device 120 is generally understood to be possessed by a respective user 110 (and thus, the personal device 120 is expected to be proximal to the user 110). A personal device 120 may execute one or more software applications, which may include a voice assistant application, a dedicated prescription management application ("Rx application"), and/or other suitable software applications. A personal device 120 may particularly include one or more visual displays (e.g., a touchscreen), one or more microphones (e.g., capable of receiving voice commands and/or other audio), and/or one or more audio output devices (e.g., a speaker or another audio port) capable of producing audible and/or inaudible sound.

The environment 100 may include one or more fixedly installed computing devices 124 ("fixed computing device"), which may include, for example, a desktop computer or a computing node of a home data system or home security system. Generally, a "fixed" computing device 124 refers to a device that is expected to remain in a same location corresponding to the user 110 (e.g., in a home or workplace of the user 110, or in a more particular location therein). A fixed computing device 124 may particularly include one or more visual displays (e.g., a touchscreen), one or more microphones (e.g., capable of receiving voice commands and/or other audio), and/or one or more audio output devices (e.g., a speaker or another audio port) capable of producing audible and/or inaudible sound.

The environment 100 may include one or more speaker devices 128 ("speaker"). The speaker 128 may generally be a device capable of producing and/or receiving audible and/or inaudible sound. In some cases, the speaker 128 is specially configured to produce, receive, and/or transmit sound, without substantially more computing capabilities. A speaker 128 may be communicatively connected to other elements of the environment 100, for example via WiFi and or Bluetooth connections. In some implementations, for example, a speaker 128 may be a smart speaker that includes one or more software applications that implement a voice assistant (e.g., Amazon Alexa).

The environment 100 may include a vehicle 136. The vehicle 136 may include a vehicle data system including one or more computing devices such as visual displays, microphones, and/or speakers. The data system of the vehicle 136 may be communicatively connected via the network 105 to other devices of the environment 100 (e.g., to a personal device 120 via Bluetooth or WiFi, and/or to the Internet via terrestrial and/or satellite communications).

The environment 100 may include one or more servers 144 ("server") that may facilitate communications among computing elements of the environment 100. The server 144 may implement prescription-related applications that facilitate performance of prescription-related actions herein via the other computing elements of the environment 100. Such prescription-related applications may, for example, provide prescription-related information, facilitate orders/refills, and/or authenticate/authorize users via techniques described herein. The server 144 may store information pertaining to prescriptions and/or users, such information including insurance information, payment information, authentication/authorization information, and/or other prescription information described herein.

Various computing elements, such as a personal device 120, computer 124, speaker 128, and/or vehicle 136, may exchange information with the server 144. Accordingly, in embodiments herein, a computing element communicating with the server 144 may be referred to as a "client device," i.e., a client in a client-server relationship with the server 144. In particular, devices in the environment 100 may exchange voice information, for example via Voice over Internet Protocol (VoIP).

Computing elements of the environment 100 generally may include at least (1) one or more processors, and (2) one or more computer memories storing non-transitory computer executable instructions that, when executed via one or more processors, cause the computing elements to perform actions described herein. In some embodiments, non-transitory computer executable instructions may be included in one or more pre-installed or downloadable software applications. Furthermore, in some embodiments, one or more non-transitory computer-readable media may store non-transitory executable instructions that, when executed via computing elements described herein, cause the computing elements to perform actions described herein.

The environment 100 may include additional or alternate elements, in some embodiments. The environment 100 may include fewer elements, in some embodiments. In particular, it should be evident that not all of the elements of the environment 100 may be required to perform any particular technique described herein.

Where similar computing elements are described in subsequent portions of this detailed description, it should be appreciated that the subsequently described computing elements may correspond to the description of similar elements in FIG. 1, unless indicated otherwise.

II. Multi-Factor Authentication for Access to Prescription Information and Functions Existing software applications may provide users access to various information and functions relating to prescriptions. Such applications may, for example, be implemented at a smartphone and allow a user to view prescription-related information, order a refill, view a status of a refill, and/or communicate with a pharmacist or doctor. However, access to prescription resources often requires confidence that the person attempting to access information or functions is a person who has been authorized to access the information or functions (e.g., a patient, a caregiver, a pharmacist, a parent/guardian, etc.). In some cases, confidence is expressed via "levels of assurance of identity," (e.g., four-level HIPAA identity assurance structure) wherein different levels of assurance permit increasingly sensitive protected health information (PHI) to be provided to a user.

"Multi-factor authentication" (MFA) generally refers to computing techniques that require two or more independent items of evidence ("factors") to authenticate a user to access a resource. Factors in MFA are broadly classified into (1) something a user knows (e.g., a password or a personal identification number (PIN)), (2) something a user has (e.g., an RFID-enabled keycard carried by the user), and (3) something a user is (e.g., fingerprint or other unique biometrics corresponding to the user). In some implementations, for example, an MFA method to access prescription-related information in a prescription application may require a user to enter a password, and subsequently enter an alphanumeric verification code transmitted by SMS text after the correct password is received. This example MFA method thus assures that a person accessing the prescription-related information is one who knows the password and is in possession of a mobile device associated with the authorized user.

Access to particular information or actions may require different levels of authentication. For example, to receive and access a notification that a prescription is ready for retrieval (where the specific name of the product is left unnamed), only a simple username and password authentication may be required. However, to actually view the name of the prescription product or to perform other actions associated with the prescription (e.g., modify a refill order), an additional factor of authentication may be required. Access to certain resources may require two, three, or more authentication factors.

Ideal MFA methods are capable of reliably producing various levels of identity assurance (i.e., few false-positives and/or false negatives) via various combinations of MFA factors. Additionally, ideal MFA methods are minimally invasive and time-consuming to users. In light of these considerations, techniques proposed herein include use of voice verification and other audio techniques for single-factor and/or multi-factor authentication for access to prescription-related resources.

In some embodiments, voice authentication may be used as a factor in access to prescription related resources). Referring to FIG. 1, voice input from a user may be received via a microphone of a personal device 120, fixed device 124, speaker 128, vehicle 136, and/or another computing device (e.g., via the network 105). Received voice input may be compared to voice data stored at the server 144 to identify the speaker from whom the voice input was received. An identified speaker may have associated access permissions to prescription-related resources, and different speakers may have different permissions. For example, while a patient or licensed caregiver may have full capability to view prescriptions, order a refill, etc., a parent or guardian of the patient may have lesser permissions.

Other audio-based authentication methods may be used in single or multi-factor authentication. For example, in some embodiments an audible or non-audible audio tone may be produced via a first electronic device and selected via a nearby second electronic device. For example, the audible or non-audible tone may be produced via a personal device 120 of the user 110, and the produced tone may be subsequently detected via a speaker 128 which is fixedly installed in a home of the patient (or vice versa). If the produced tone is detected via the speaker 128, the detection of the tone indicates that the user 110 is located in the home of the patient, and thus confidence is established that the user 110 is a person authorized to access the prescription resource (e.g., a patient or an at-home caregiver).

In some embodiments, types of prescription resources made available to a user may be adaptive to the level of identity assurance achieved via the techniques descried herein (e.g., based upon a HIPAA assurance level achieved). For example, a process for setting a prescription refill location may be adaptive to the authentication level achieved. If the user has obtained a first authentication level, for example, a graphical user interface and/or an audio output may prompt the user to indicate whether the user wishes to pick up the prescription refill "at the same location as last time" (i.e., without specifically identifying the location). If the user has achieved (or subsequently achieves) a second, higher authentication level (e.g., via one or more additional authentication factors), the graphical user interface and/or audio output may provide further information specifically identifying the retrieval location by names and/or address (and/or additional protected health information corresponding to the authentication level achieved.

III. Communication Mode Selection Based Upon Device Context

Providing prescription-related resources via electronic computing devices typically includes various interaction with a user thereof (e.g., patient, caregiver, etc.). For example, a process of ordering a prescription refill may include at least steps of (1) indicating a desire to refill a prescription, (2) signing in and/or otherwise authenticating for access to prescription resources, (3) indicating a prescription to refill, (4) identifying a time and/or location (e.g., pharmacy) for the refill, and/or (5) providing doctor and/or payment information.

As will be described herein, steps for accessing prescription-related resources may be completed via a variety of modes of interactive communication with the user ("communication modes" or simply "modes"), which may for example include touchscreen GUI interactivity, voice interactivity, and/or other suitable modes of communication and/or interaction. In some cases, a dedicated prescription application or other application may provide for any particular step or action to be completed via any one of two or more available modes. Particularly, voice interactivity (i.e., one or more voice interactions) for performing any particular step may be implemented via a voice-enabled virtual assistant program ("voice assistant"). Generally, voice interactions as described herein include receiving voice input from the user via a device microphone and/or providing audio output via a device speaker. Although some users may prefer using voice interactivity to perform certain steps, voice interactions may not be feasible in certain circumstances, for example (1) when a user's electronic device is not capable of supporting such interactions (e.g., lacking the required software and/or hardware), and/or (2) when the user is not in a quiet or private environment, which may thereby present noise interference and/or risk compromising protected health information).

Accordingly, techniques may be used to intelligently select a communication mode for use in accessing/providing a prescription resource. In particular, systems and methods may determine the communication mode based upon information associated with one or more electronic devices via which the user attempts to access the prescription resource.

A mode of communication may, for example, be selected by a prescription application based upon one or more characteristics of the electronic device via which a user accesses a prescription resource. The electronic device of the user may, for example, provide configuration information of the electronic device that (1) indicates whether the electronic device is outfitted with a screen, microphone, and/or speaker, and/or (2) indicates whether the user has provided necessary permissions for a prescription application to utilize the screen, microphone, and/or speaker. If the device lacks a microphone, for example (or if the user has not granted microphone permissions to the prescription application), the prescription application may determine that a resource should be provided via touchscreen interactions instead of voice interactions. Conversely, if the user's device lacks a screen (e.g., the user is accessing prescription information via a voice request from a speaker), the prescription application may provide the same resource via audio output.

IV. Communication Mode Selection Based Upon User Context

Further to the above, a communication mode for use in accessing/providing a prescription resource may be additionally or alternatively be selected based upon information associated with a "user context" defining a situation in which the user attempts to access the prescription resource.

The mode may be selected, for example, based upon detected background noise in an environment of the user. Referring again to FIG. 1, background noise level may be determined based upon audio received via a device near to a user 110 (e.g., personal device 120, fixed device 124, and/or speaker 128). Based upon the background noise level exceeding a threshold, it may be determined, for example, that the user 110 is in a in a noisy and/or public environment (e.g., a crowded street, restaurant, or stadium). When noise exceeds the threshold, it may be determined that a prescription resource should not be access via voice input from the user 110 (e.g., because a device may have difficulty obtaining reliable voice input from the user, and/or because the voice input may be overheard by others in the environment, thereby compromising protected health information). Similarly, when noise exceeds a threshold, it may be determined that a prescription resource should not be provided via audio output (e.g., because the output may be difficult to hear, and/or because the audio output may be overheard by others difficult to keep private from others in the user's environment). In some embodiments, the placement of the user in a public setting may allow for at least some medical information to be shared via a voice interaction, but may not allow for other more sensitive protected health information to be provided.

Figure 2:
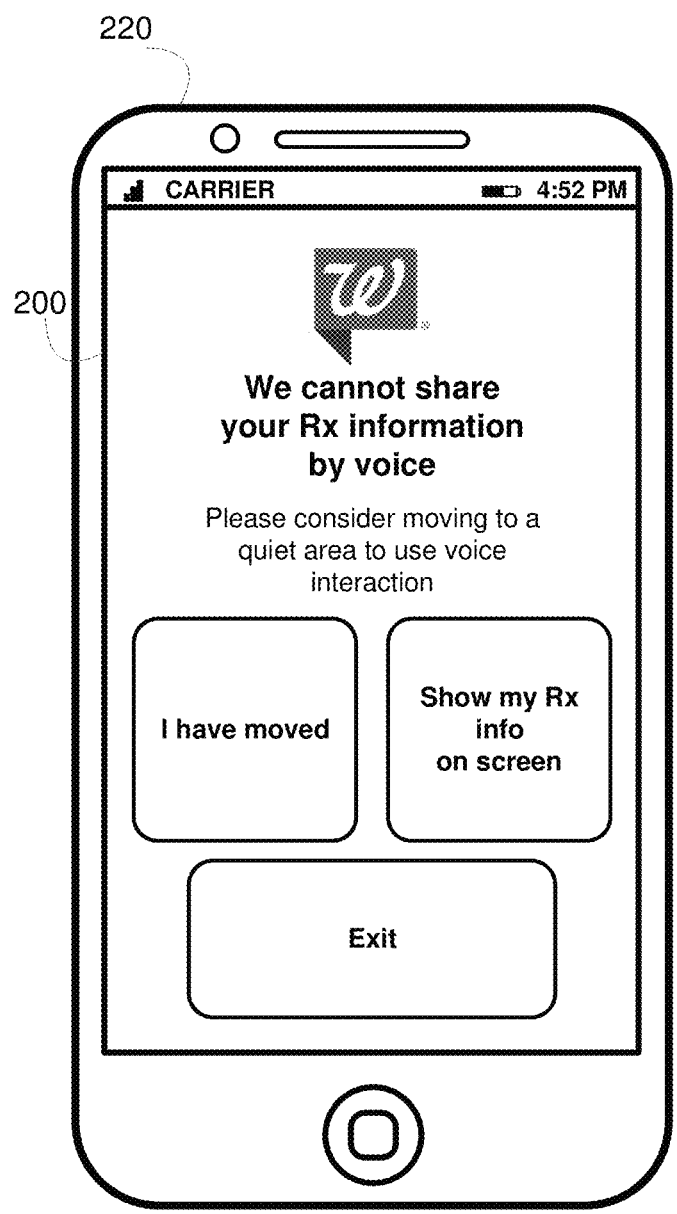
FIG. 2 depicts an example graphical user interface that may be displayed via an electronic computing device of a user, in accordance with some embodiments.

In some embodiments, an indication of the detected background noise may be provided to user attempting to access a prescription resource via voice interactivity. FIG. 2 depicts an example graphical user interface (GUI) 200 that may be provided to the user of an electronic device 220 based upon a determination that background noise exceeds a threshold. The device 220 may be, for example, a personal device 120, fixed computing device 124, vehicle 136, and/or another suitable one of the client devices described with respect to FIG. 1. As shown in FIG. 2, the interface 200 may include controls that allow the user to (1) indicate that the user has moved to quieter area and thus can access a prescription resource via voice/audio interactions (e.g., upon re-determination of the background noise level), (2) indicate that the user prefers to use another mode of interaction (e.g., visual touchscreen interactions), and/or (3) exit the process of accessing the prescription resource.

Background noise as described above may be determined, for example, via a dedicated prescription application installed at one or more electronic devices associated with the user. A user may, for example, provide permission for the prescription application to record audio at the electronic device 220 (e.g., background audio permissions) and/or via another one or more electronic devices (e.g., other speakers/microphones in the user's home).

In some embodiments, the communication mode may be selected based upon other information indicative of the user's ability to conduct certain types of interactions. For example, when a user is driving, it may not be safe for the user to use touchscreen interactions to access a prescription resource. Location and/or acceleration information may be received via an electronic device corresponding to the user (e.g., from a personal device 120 or a data system of a vehicle 136. Based upon the received information, it may be determined whether the user is driving a vehicle. If the user is driving, steps for accessing a prescription resource may instead be performed via voice and/or other audio interactions via one or more electronic devices of the user (e.g., via the personal device 120 or vehicle 136).

In some embodiments, a communication mode may be selected upon analysis of voice input provided by the user. In particular, voice sentiment analysis may be utilized to determine a user's sentiment regarding an attempt to access a prescription-related resource. If, for example, the user exhibits frustration with refilling a prescription via a voice assistant, it may be determined that subsequent steps of a refilling process are to be completed via touchscreen interactions instead of voice interactions. Accordingly, a voice assistant and/or GUI may inform the user of the selection of the new mode for completion of the refilling process.

A communication mode for providing prescription resources may additionally or alternatively be selected based upon one or more other steps that a user has already completed. For example, if a process of refiling a prescription requires entering a street address or insurance information of the patient, a touchscreen interaction may be preferred. If, however, the entering of the street address or insurance information has already been completed (e.g., previously obtained/saved from the user), a voice interaction may be selected for any remaining steps.

Still other information corresponding to the user may be considered in selection of a communication mode, in some embodiments. For example, a communication mode may be selected based at least in part upon demographic information corresponding to the user. Additionally, or alternatively, a prescription application may store user preferences and/or usage information indicative of the user's preferred modes of interaction. A user may, for example, favor or disfavor interactions with a voice assistant over touchscreen interactions to access prescription resources.

V. Customizable Voice Interactions for Prescriptions

As described herein, many users prefer to perform access prescription-related resources via voice interactions. However, voice interactions in the context of prescriptions in particular face additional challenges.

For one, although many patients know the basic purpose of their medication or a brand name corresponding to the medication, a patient may be less likely to successfully remember or pronounce a generic name of the drug that the patient is prescribed. For example, a patient may seek to refill their prescription of atorvastatin (a cholesterol-lowering medication). Although the patient may be able to provide voice input stating the purpose of their medication (e.g., "reorder my cholesterol medication" or "refill my heart pills") or even a particular brand name of a drug containing the same active ingredient (e.g., Lipitor), the patient may be less likely to actually state the generic name atorvastatin (e.g., "refill my atorvastatin"). Similarly, if the patient wishes to schedule and receive timed reminders to take their atorvastatin, the reminders may be more effective if the reminders use terms familiar to the patient (which may not include the generic drug name).

Accordingly, systems and methods may receive and intelligently analyze voice input to determine an intent associated with the voice input (e.g., refilling a prescription). Voice input may be received from the user, for example, via a personal device 120, fixed device 124, speaker 128, and/or vehicle 136 of FIG. 1. Based upon the received voice input, one or more servers (e.g., server 144 of FIG. 1) may intelligently identify one or more prescriptions and/or prescription products to which the voice input corresponds. A server may, for example, store information including various alternative words that may correspond to a same prescription product (e.g., for atorvastatin, words such as "heart," "cholesterol," "pill," and "Lipitor"). The server may also store information identifying prescriptions corresponding to patients, such that received voice input can be compared to prescriptions corresponding to the user from whom the voice input was received.

By analyzing the received voice input, the server may identify a prescription and/or product to which a request pertains, and the server may accordingly provide a response to the user. Thus, a voice request from a user can be fulfilled even if the user does not state the generic name of their prescription. In some circumstances, two or more prescriptions may correspond to a request from the user. For example, a patient having two or more prescriptions may say "refill my prescription." Based upon this request, a user interface may be provided to the patient, the interface displaying options to refill each one of the two or prescriptions corresponding to the patient. In some embodiments, the two or more prescriptions corresponding to the patient may be further narrowed to only include prescriptions filling one or more criteria (e.g., prescriptions that are eligible and/or authorized for a refill).

Figure 3:
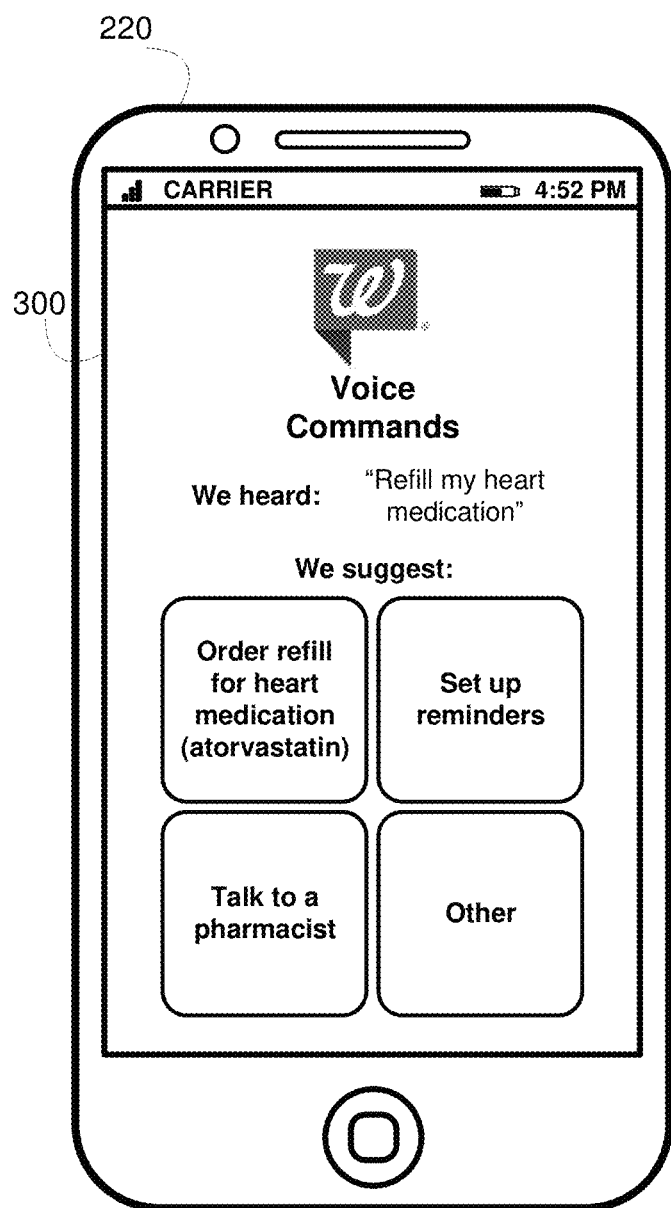
FIG. 3 depicts another example graphical user interface that may be displayed via an electronic computing device of the user, in accordance with some embodiments.

FIG. 3 depicts an example graphical user interface (GUI) 300 that may be provided via the device 220 in accordance with the above. In response to detection of voice input including "heart medication," the GUI 300 may provide interactive controls to reorder the drug atorvastatin and/or perform other tasks associated with the atorvastatin prescription. In some embodiments, access to information displayed via the graphical user interface 300 may further be mediated through use of authentication techniques described in this detailed description.

As described above, many patients and caregivers prefer to receive timed reminders to use their prescription products. Such reminders may be provided in various forms, such as phone calls, text messages, push notifications, and/or audio reminders. In any case, though, because a patient is not always familiar with the generic name of their prescription product (e.g., atorvastatin), reminders that rely upon the patient recognizing the generic name of a prescription product may not always be effective.

Thus, systems and methods are proposed to allow users to customize and/or pre-record audio reminders for consuming prescription products. In some embodiments, a user may select from a list of pre-recorded reminders that each correspond to a same prescription product, but include different audio. One reminder, for example, may include a generic drug name ("take your atorvastatin, one pill", and another may instead include a purpose of the drug (e.g., "take your heart medication, one pill"). Additionally or alternatively, in some embodiments, a user may record personalized audio via a microphone of their electronic device. Personalized audio may be received and analyzed via one or more servers to verify that the audio (1) sufficiently corresponds to the prescription product for which the reminder is intended (e.g., the audio states at least the purpose of the drug, the generic name, and/or other similar terminology as described above), (2) is clear (i.e., is not excessively noisy such that a patient may not clearly hear the audio upon replaying, and/or (3) excludes PHI or certain portions thereof (e.g., for if the reminder is to be played without the user needing to provide multi-factor authentication upon each reminder). Upon verification that the personalized audio is appropriate, the personalized audio may be stored and subsequently played via one or more electronic devices of the user (e.g., personal device 120, speaker 128, etc.) at scheduled times to remind the user to consume or administer a prescription product.

In some embodiments, a reminder may exclude certain protected health information. For example, a reminder may simply notify the user that a reminder is available, and the user may be required to provide authentication before the full customized and/or pre-recorded audio is provided to the user.

Figure 4:
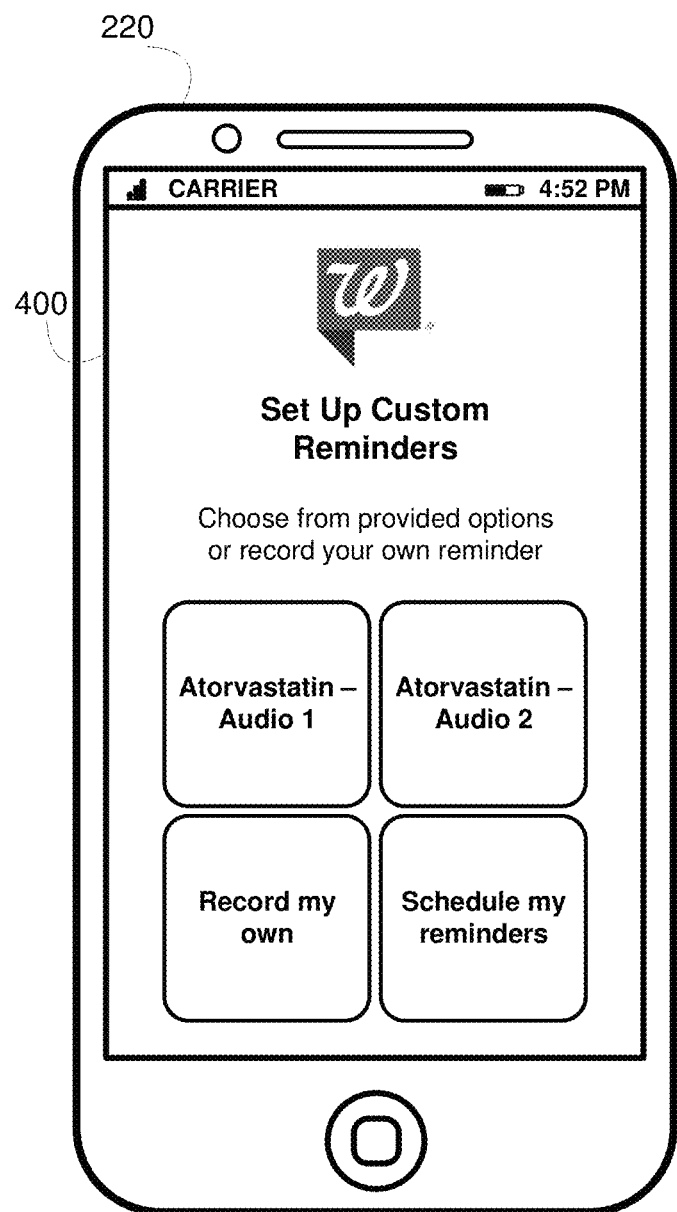
FIG. 4 depicts still another example graphical user interface that may be displayed via an electronic computing device of the user, in accordance with some embodiments.

FIG. 4 depicts an example graphical user interface (GUI) 400 that may be provided via the device 220 in accordance with the above. The GUI 400 may allow the user to choose among a plurality of audio reminders for use in reminding the user to consume or administer a same prescription product. The GUI 400 may further allow the user to select to record their own personalized audio, selection of which may activate a microphone of the electronic device to record audio. Additional graphical user interfaces may be envisioned, in various embodiments.

VI. Example Electronic Computing Device

Figure 5:
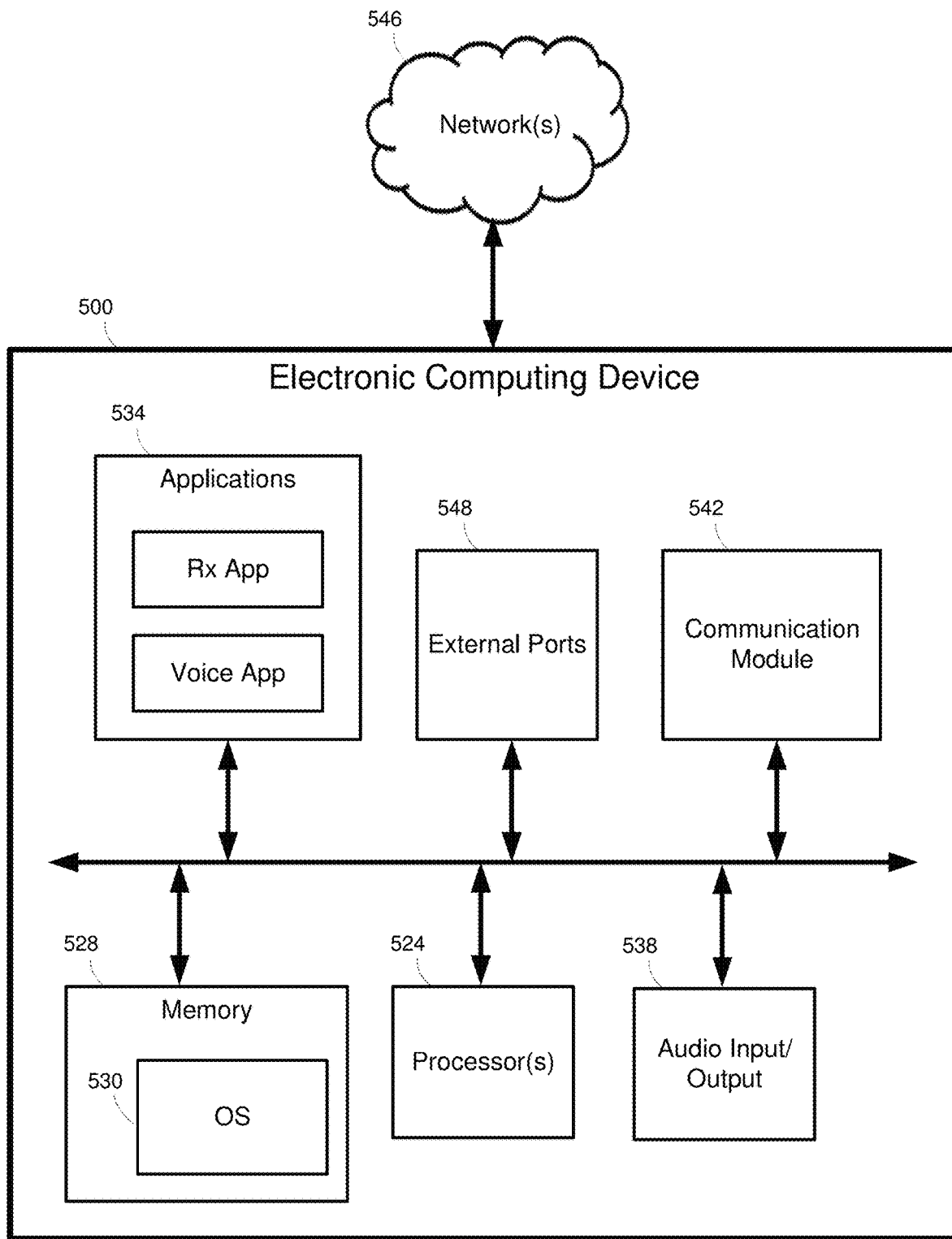
FIG. 5 depicts an example electronic computing device that may implement at least some of the techniques described herein, in accordance with some embodiments.

FIG. 5 depicts a diagram of an example electronic computing device 500 that may implement at least some of the techniques described herein. The electronic computing device 500 may correspond, for example, to one or more of the computing devices depicted in FIG. 1 (e.g., personal device 120, fixed computing device 124, speaker 128, and/or data system of a vehicle 136). Different implementations of the device 500 may have different components and/or capabilities, and accordingly, the device 500 may include additional, alternate, and/or fewer computing components to those described herein.

The example device 500 may include a processor 524 (i.e., one or more processors) and a memory 528 (i.e., one or more computer memories). The memory 528 may store an operating system 530 capable of facilitating functionalities of the device 500 described herein. The device 500 may store a set of applications 534 (e.g., each corresponding to one or more sets of non-transitory computer executable instructions). Such applications may include, for example, a dedicated prescription application ("Rx App") and/or a voice assistant application ("Voice App") configured to implement functionalities described herein.

The processor 524 may interface with the memory 528 to execute the operating system 530 and the set of applications 534. The memory 528 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others.

The device 500 may include audio input/output 538, which may include one or more speakers and/or one or more microphones capable of producing and receiving audio, respectively. The device 500 may include various other input/output modules, such as a touchscreen, camera, keyboard, mouse, touchpad, etc.

The device 500 may further include a communication module 542 (i.e., one or more communication modules) configured to communicate data via one or more networks 546 (e.g., the network(s) 105 described with respect to FIG. 1). In some embodiments, the communication module 542 may include one or more transceivers (e.g., WWAN, WLAN, and/or WPAN transceivers) functioning in accordance with IEEE standards, 3GPP standards, or other standards, and configured to receive and transmit data via one or more external ports 548. For example, the communication module 542 may transmit and/or receive voice data via Voice over Internet Protocol (VoIP).

In general, a computer program product in accordance with an embodiment may include a computer usable storage medium (e.g., standard random access memory (RAM), an optical disc, a universal serial bus (USB) drive, or the like) having computer-readable program code embodied therein, wherein the computer-readable program code is adapted to be executed by the processor 524 (e.g., working in connection with the operating system 530) to facilitate the functions as described herein. In this regard, the program code may be implemented in any desired language, and may be implemented as machine code, assembly code, byte code, interpretable source code or the like (e.g., via Python, or other languages, such as C, C++, Java, ActionScript, Objective-C, JavaScript, CSS, XML). In some embodiments, the computer program product may be part of a cloud network of resources.

VII. Example Computer-Implemented Methods

FIGS. 6-10 depict flow diagrams of example computer-implemented methods, in accordance with some embodiments. The actions of the methods described with respect to FIGS. 6-10 may be performed, for example, via computing entities described with respect to FIGS. 1 and/or 5. For example, with reference to FIG. 1, actions of the methods may be performed via one or more servers 144 (e.g., via one or more processors thereof, executing non-transitory computer executable instructions stored in memory of the one or more servers 144). Additionally or alternatively, at least some actions of the methods of FIGS. 6-10 may be performed by one or more client devices (e.g., by a personal device 120, fixed computing device 124, speaker 128, and/or data system of a vehicle 136). Furthermore, in some embodiments, one or more non-transitory computer readable media may store instructions that, when executed via one or more processors, cause one or more computing devices to perform actions of the methods of FIGS. 6-10.

Where appropriate, methods of FIGS. 6-10 may include additional, fewer, and/or alternate actions. For example, the methods of each of FIGS. 6-10 may further include actions described with respect to other ones of the methods of FIGS. 6-10. Order of actions described herein may vary, in accordance with various embodiments.

Figure 6:
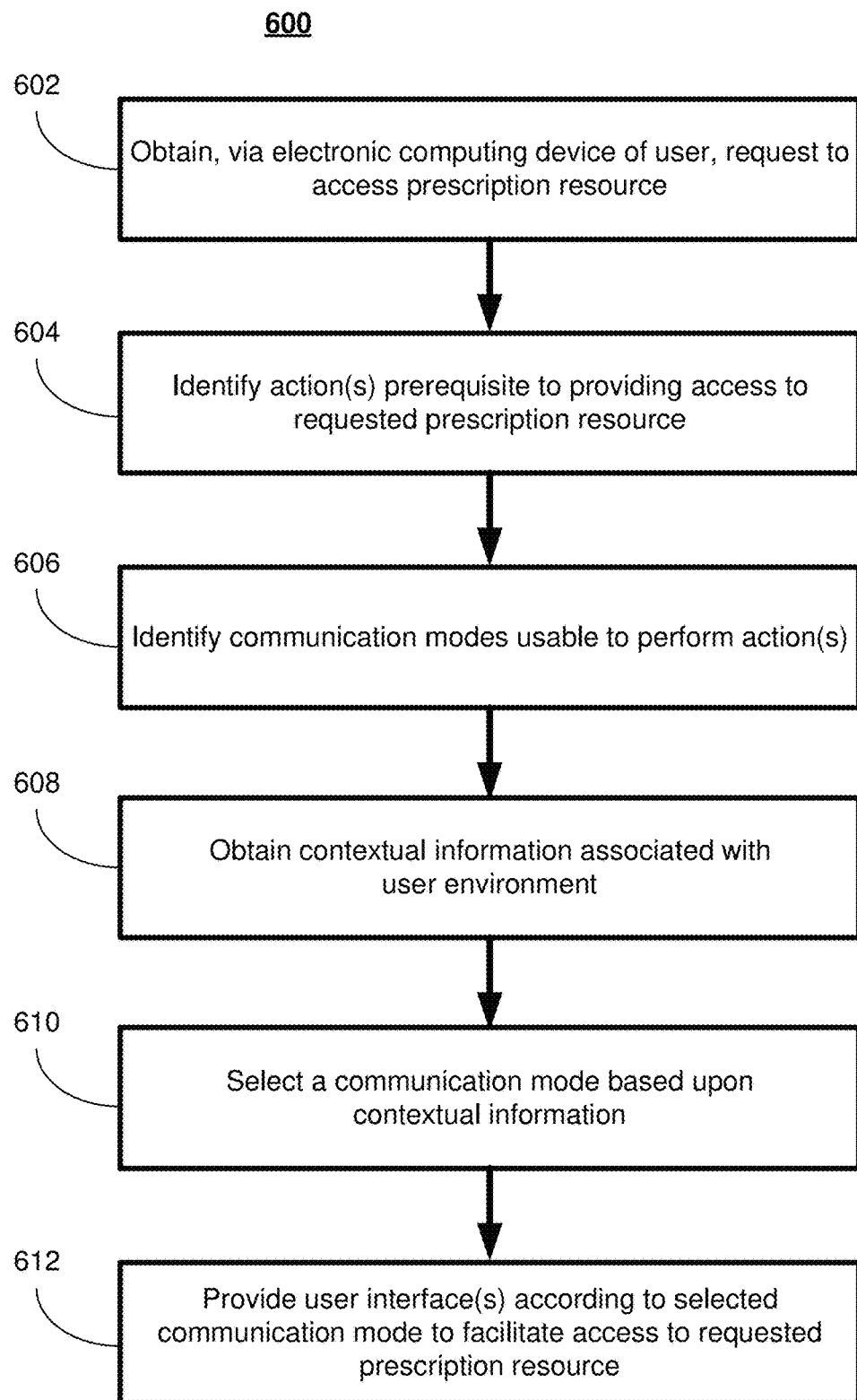
FIG. 6 depicts an example computer-implemented method, in accordance with some embodiments.

Referring first to FIG. 6, an example computer-implemented method 600 is provided for selecting a communication mode to facilitate user access to a prescription resource (e.g., access to protected health information or other prescription-related information, and/or access to a prescription-related action such as obtaining a prescription product, ordering a prescription refill, viewing a status of a refill, etc.).

The method 600 includes obtaining an indication of a request to access the prescription resource (602). Particularly, the request may be obtained via an electronic computing device of a user. More particularly, the request may be obtained via a prescription application executing at the electronic computing device. The user may be a patient, guardian, caregiver, etc., and the electronic computing device may be, for example a smartphone, tablet, and/or other suitable computing device described herein.

The method 600 includes identifying one or more actions prerequisite to providing access to the requested prescription resource to the user (604). The one or more actions may include, for example, (1) user authentication to access the resource (e.g., via a password, PIN, voice signature, etc.), (2) specifying a prescription, and/or (3) providing/verifying of information by the user (e.g., required address or insurance information prerequisite to refilling a prescription). In any case, the one or more actions may require completion prior to certain information/functionalities being made available to the user.

The method 600 additionally includes identifying one, two, or more communication modes usable to perform the one or more actions (606). The communication modes may, for example, be different forms of user interaction via which information is provided to the user and/or received form the user (e.g. graphical user interface (GUI) touchscreen interaction, voice interaction, other forms of audio interaction, etc.). As an example, a prerequisite of verifying a pharmacy of the user for a prescription refill may be conducted via a GUI interactions, voice interactions, and/or other communication modes. As another example, a prerequisite action of authentication may be performed via GUI interactions (e.g., entering a password) or via voice interactions (speaker verification). In some circumstances, only one communication may be available for certain actions (e.g., if voice authentication is specifically required and other authentication forms cannot be used, voice interactions may be required).

The method 600 further includes obtaining contextual information associated with an environment in which the user is located (608). Contextual information may include, for example, accelerometer data and/or location data of the user's electronic computing device or another device. Additionally or alternatively, contextual information may include audio data (e.g., captured via the electronic computing device) indicative of background noise in the user's environment).

The method 600 still further includes selecting a particular communication mode from two or more communication modes (610). Particularly, the communication mode may be selected based upon the obtained contextual information. If, for example, the user is driving (e.g., as indicated by location/accelerometer data), audio communication modes may be chosen (e.g., voice interactions with the user). As another example, visual communication modes may be chosen based upon the background noise in the user's environment, or the user may be prompted to move into a quieter, more private area before using an audio communication mode (e.g., upon obtaining more audio data to verify the noise level).

The method 600 further includes providing one or more interactive user interfaces to the electronic computing device in accordance with the selected communication mode (612, e.g., voice interface(s), graphical user interface(s), etc.). The provided user interface(s) may generally facilitate the user's access to the requested prescription resource (e.g., the requested information or functionality).

Figure 7:
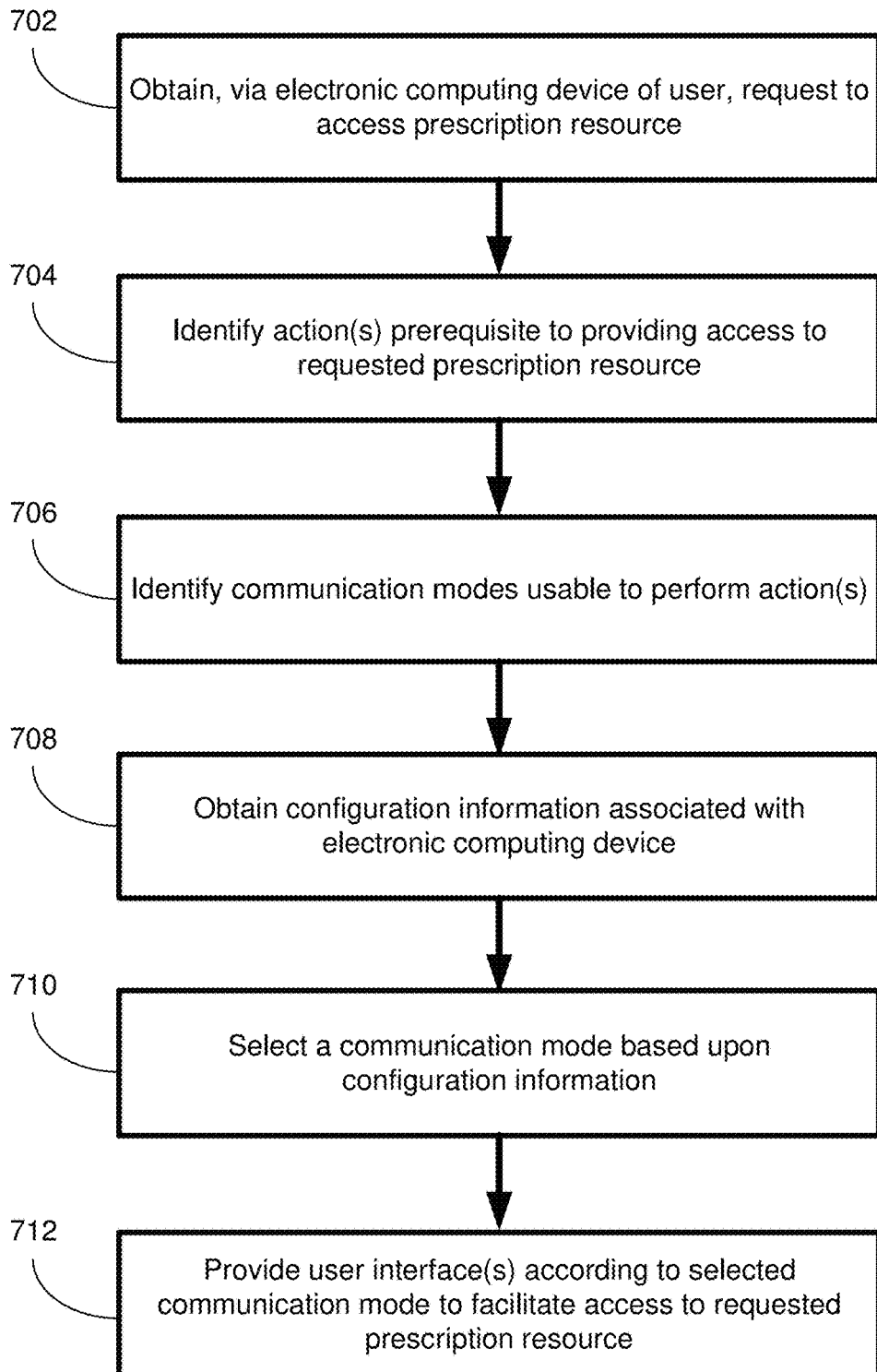
FIG. 7 depicts another example computer-implemented method, in accordance with some embodiments.

Now referring to FIG. 7, another example computer-implemented method 700 is provided for selecting a communication mode to facilitate user access to a prescription resource (e.g., access to prescription information and/or functionalities).

The method 700 includes obtaining an indication of a request to access the prescription resource (702). The request may be obtained via an electronic computing device of a user (e.g., a smartphone executing a prescription application).

The method 700 also includes identifying one or more actions prerequisite to providing access to the requested prescription resource to the user (704). The one or more actions may include, for example, include any of the actions described above with respect to FIG. 6, and/or other suitable actions described herein. In any case, the one or more actions may require completion prior to certain information/functionalities being made available to the user. The method 700 additionally includes identifying one, two, or more communication modes usable to perform the one or more actions (706, e.g., GUI communications, voice communications, other audio communications, etc.).

The method 700 further includes obtaining configuration information associated with the electronic computing device of the user (708). Configuration information may include, for example (1) information indicating hardware components included in or otherwise operatively connected to the electronic computing device (e.g., indicating presence of a touchscreen, speaker, microphone, or camera, or lack thereof), and/or (2) information indicating permissions granted or denied to software applications executing via the electronic computing device (e.g., permissions of a prescription application to access the microphone, speaker, touchscreen, camera, etc.).

The method 700 still further includes selecting a particular communication mode from two or more communication modes (710). Particularly, the communication mode may be selected based upon the obtained configuration information. If, for example, the electronic computing device does not include a microphone, a visual communication mode may be selected. If the electronic device has a microphone but the user has denied access to the microphone by a required application (e.g., by a prescription application), a visual communication mode may similarly be selected.

The method 700 further includes providing one or more interactive user interfaces to the electronic computing device in accordance with the selected communication mode (712, e.g., voice interface(s), graphical user interface(s), etc.). The provided user interface(s) may generally facilitate the user's access to the requested prescription resource (e.g., the requested information or functionality).

Figure 8:
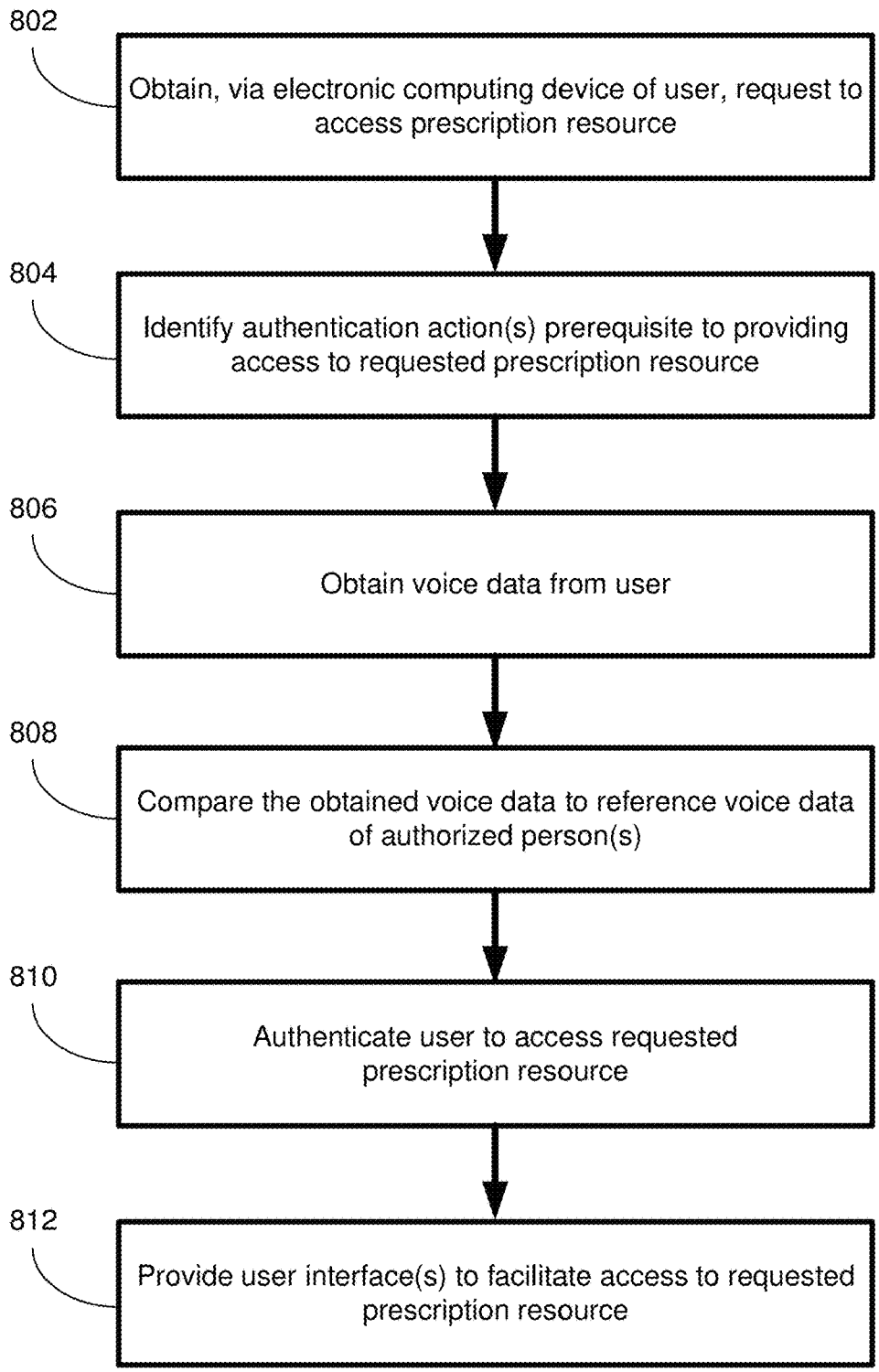
FIG. 8 depicts yet another example computer-implemented method, in accordance with some embodiments.

FIG. 8 depicts an example computer-implemented method 800 for authenticating a user to access a prescription resource. The method 800 includes obtaining an indication of a request to access the prescription resource (802). Particularly, the request may be obtained via an electronic computing device of a user (e.g., a smartphone executing a prescription application).

The method 800 also includes identifying an authentication action prerequisite to providing access to the requested prescription resource (804). The authentication may include, for example, providing a PIN, providing a password, performing a voice verification, and/or other forms of authentication described herein.

The method 800 further includes obtaining voice data corresponding to the user (806). Particularly, the voice data may be obtained via a microphone of the electronic computing device. The voice data may be compared to reference voice data corresponding to one or more persons authorized to access the requested prescription resource (808, e.g., a patient, a caregiver, etc.). Based upon the comparison (e.g., when the speaker matches a person authorized to access prescription-related information and/or functionalities), the user may be authenticated to access the resource (810).

In various embodiments, the method 800 may include combinations of authentication techniques. For example, in some embodiments, the one or more authentication actions may include reciting a PIN, and speaker verification may be used in combination with verification of the recited PIN by the user. The user may be authenticated based upon both the PIN and speaker being authenticated. Still further, other forms of verification may be used in combination with voice-based techniques (e.g., push-notification verification, entry of a PIN or password via a GUI, etc.).

In some embodiments, multiple persons may have different authorizations to access information and/or functionalities on behalf of a same patient. That is, each of the multiple persons has at least some authorizations, but the extent of the authorizations may vary. In these embodiments, the method 800 may include determining the level of authorization associated with the authenticated user. User interfaces provided via the method 800 may be modified to include and/or exclude certain protected health information and/or other content, in accordance with the level of authorization of the authenticated user.

In any case, upon authentication of the user, one or more user interfaces may be provided to the electronic device to facilitate access to the requested prescription resource (812). The one or more interfaces may include, for example, a voice interface, graphical user interface, and/or other interfaces described herein.

Figure 9:
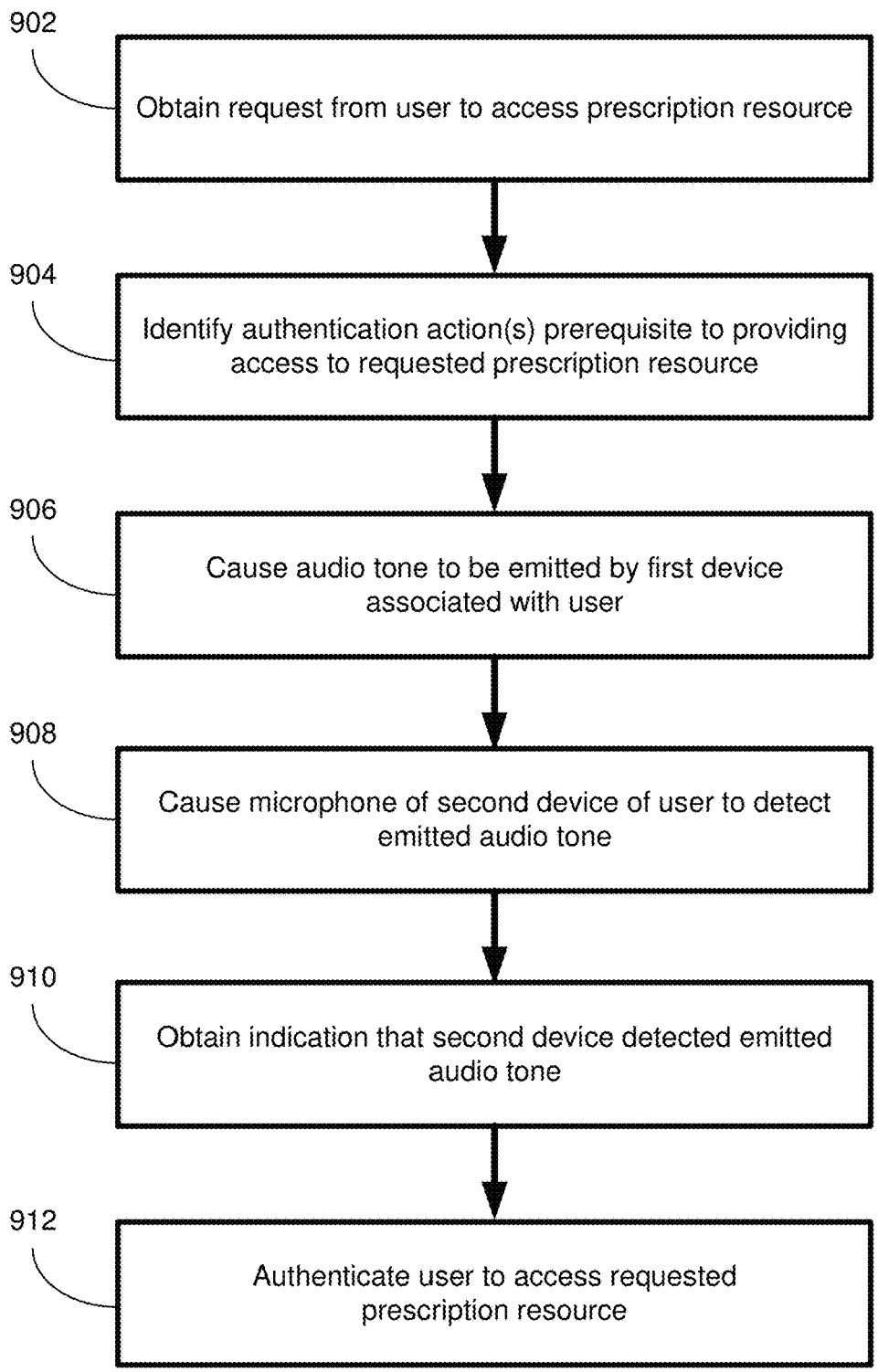
FIG. 9 depicts still another example computer-implemented method, in accordance with some embodiments.

Now referring to FIG. 9, an example computer-implemented method 900 is provided for authenticating a user to access a prescription resource. The method 900 includes obtaining an indication of a request to access the prescription resource (902, e.g., to obtain prescription information, order a refill, etc.). The request is associated with a user, e.g., a smartphone user. The method 900 also includes identifying an authentication action prerequisite to providing access to the requested prescription resource (904). That is, at least some authentication of the user is required to access the resource.

The method 900 further includes causing an audio tone to be emitted by a speaker of a first electronic computing device associated with the user (906), and causing a microphone of a second electronic computing device associated with the user to detect the emitted audio tone (908, e.g., via activating the microphone after the tone is emitted). That is, the actions 906 and 908 are performed via two (or more) electronic devices associated with the user (e.g., a combination of a smartphone, a tablet, a speaker, etc.). The tone may be audible or non-audible (i.e., non-audible to humans). When an indication is received that the second device detected the emitted audio tone (910), it may be determined that the first and second devices of the user are located near each other, and thus an identity of the user can be determined (e.g., as a person owning the two electronic devices). Thus, the actions above may be used as a factor in authenticating the user to access the resource.

Based at least in part upon the detection of the emitted audio tone, the user may be authenticated to access the requested prescription resource (912). In some embodiments, this authentication is used in combination with other forms of authentication described herein (e.g., voice authentication, authentication via entering information in a GUI, etc.). In any case, the method 900 may further include providing one or more user interfaces (e.g., audio, voice, and/or visual interfaces) to the user to facilitate access to the requested prescription resource.

Figure 10:
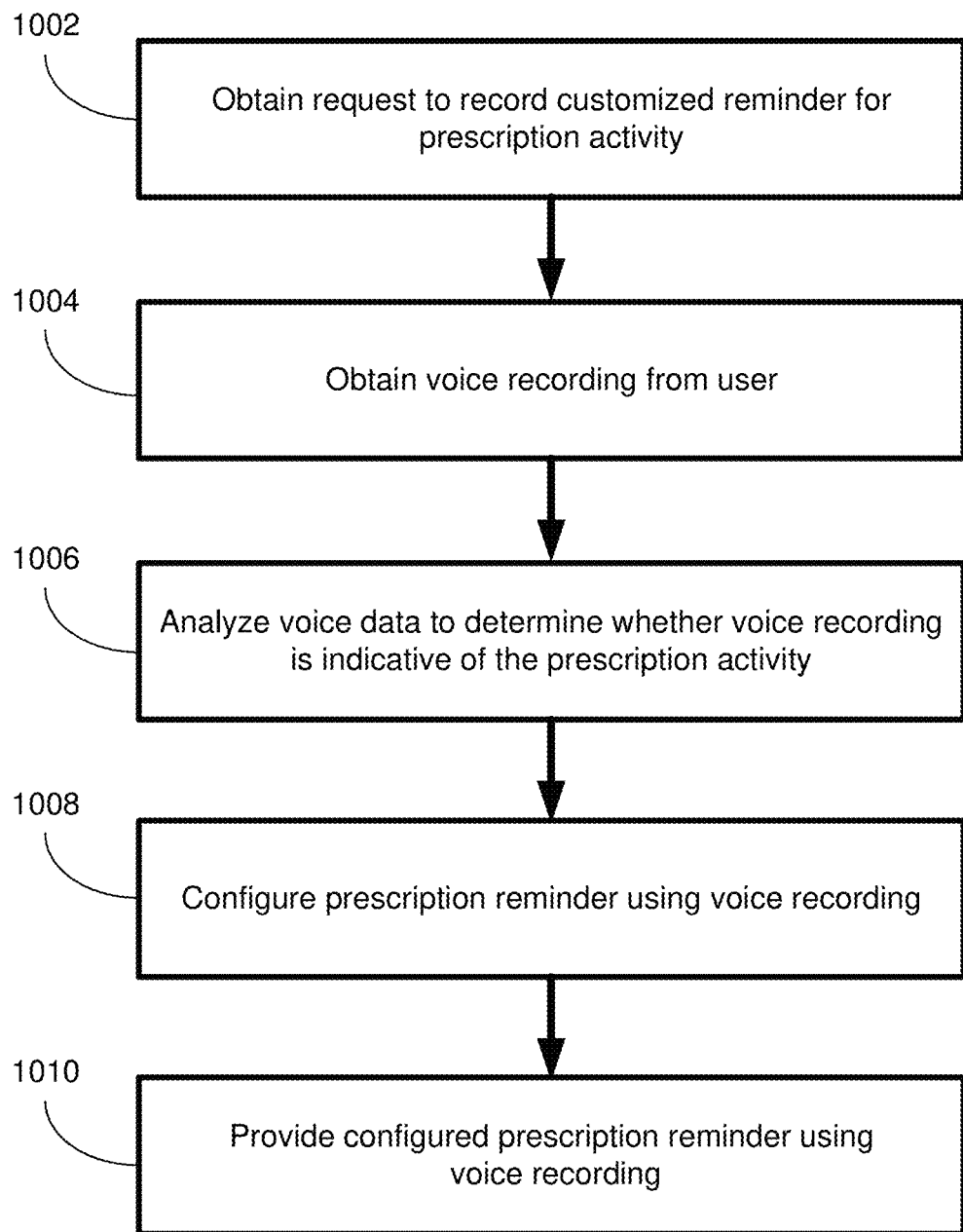
FIG. 10 depicts another example computer-implemented method, in accordance with some embodiments.

Moving to FIG. 10, an example computer-implemented method 1000 is provided for configuring a reminder associated with a prescription product. The method 1000 may include obtaining an indication of a request to record a customized reminder to perform an activity associated with the prescription product (1002). The activity may, for example, include consuming, administering, or reordering the prescription product. The request may be provided, for example, via an electronic computing device of a user (e.g., via a prescription application at a smartphone or tablet). In some embodiments, the request to record the customized reminder is selected from among other options including pre-recorded audio reminders (e.g., as shown in FIG. 4).

The method 1000 also includes obtaining a voice recording from the user (1004). The user may provide the voice recording, for example, via the microphone of the electronic computing device or via another electronic computing device. The method 1000 further includes analyzing the obtained voice recording to determine whether the voice recording is indicative of the activity for which the reminder is intended (1006). For example, if the reminder is intended to be a reminder to consume heart medication, the voice recording should at least indicate the name or purpose of the prescription product to be consumed. In response to determining that the voice recording is indicative of the activity, the reminder may be configured using the obtained voice recording (1008).

Accordingly, the method 1000 includes subsequently providing the prescription reminder at the electronic computing device of the user (1010). Particularly, providing the reminder includes causing the voice recording to be emitted by a speaker of the electronic computing device. Providing the reminder may include providing other information, in various embodiments (e.g., additional audio output and/or graphical user interfaces).

VIII. Additional Considerations

Although the above text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments could be implemented, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that may be permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a processor or other programmable processor) that may be temporarily configured by software to perform certain operations. It should be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a processor configured using software, the processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it may be communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment, or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment may be included in at least one embodiment. The appearances of the phrase "in one embodiment" in various places in the specification are not necessarily all referring to the same embodiment.

As used herein, the terms "comprises," "comprising," "may include," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also may include the plural unless it is obvious that it is meant otherwise.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed:

1. A computer-implemented method for authenticating a user to access a prescription resource, the method comprising:
    obtaining, via one or more processors, an indication of a request to access the prescription resource, the request obtained via an electronic computing device associated with a user;
    obtaining, via the one or more processors, access permission information defining different respective permission sets of a plurality of persons to access prescription resources associated with the patient, the prescription resources including the requested prescription resource;
    identifying, via the one or more processors, an authentication action prerequisite to providing access to the requested prescription resource;
    identifying, via the one or more processors, a plurality of modes of communication modes usable to perform the authentication action;
    selecting, via the one or more processors, a particular communication mode for performing the authentication action, the selecting of the particular communication mode comprising selecting a voice-based authentication, and the selecting being based upon at least one of (1) configuration information indicating compatibility of the electronic computing device to utilize each of the plurality of communication modes, or (2) contextual information indicating an environment in which the user is located;
    obtaining, via the one or more processors, voice data corresponding to the user, the voice data provided by the user via a microphone of the electronic computing device;
    comparing, via the one or more processors, the obtained voice data to reference voice data corresponding to each of the plurality of persons;
    via the one or more processors and based upon the comparison, identifying the user as a particular one of the plurality of persons;
    based upon the identifying of the user, authenticating, via the one or more processors, the identified user to access the requested prescription resource based upon the corresponding permission set for the identified user wherein authenticating the identified user to access the requested prescription resource includes using the comparison of the voice data in combination with one or more further authentication factors; and
    providing, via the one or more processors, one or more user interfaces to the electronic computing device to facilitate access to the requested prescription resource for the authenticated user.

2. The computer-implemented method of claim 1, wherein providing the one or more user interfaces comprises providing an interactive voice interface to the electronic computing device.

3. The computer-implemented method of claim 1, wherein providing the one or more user interfaces comprises providing an interactive graphical user interface to the electronic computing device.

4. The computer-implemented method of claim 1, wherein the authenticated user is at least one of a parent, guardian, or caregiver of the patient corresponding to the prescription resource.

5. A computing system configured to for authenticate a user to access a prescription resource, the computing system comprising:
    one or more processors; and one or more memories storing non-transitory computer executable instructions that, when executed by the one or more processors, cause the computing system to:
    obtain an indication of a request to access the prescription resource, the request obtained via an electronic computing device associated with a user;
    obtain access permission information defining different respective permission sets of a plurality of persons to access prescription resources associated with the patient, the prescription resources including the requested prescription resource;
    identify an authentication action prerequisite to providing access to the requested prescription resource;
    identify a plurality of modes of communication modes usable to perform the authentication action;
    select, from the usable communication modes, a particular communication mode for performing the authentication action, the selecting of the particular communication mode comprising selecting a voice-based authentication, and the selecting being based upon at least one of (1) configuration information indicating compatibility of the electronic computing device to utilize each of the plurality of communication modes, or (2) contextual information indicating an environment in which the user is located;
    obtain voice data corresponding to the user, the voice data provided by the user via a microphone of the electronic computing device;
    compare the obtained voice data to reference voice data corresponding to each of the plurality of persons;
    based upon the comparison, identify the user as a particular one of the plurality of persons;
    based upon the identifying of the user, authenticate the identified user to access the requested prescription resource based upon the corresponding permission set for the identified user wherein the authentication based upon the comparison of the voice data is used in combination with one or more further authentication factors to authenticate the identified user to access the requested prescription resource; and
    provide one or more user interfaces to the electronic computing device to facilitate access to the requested prescription resource for the authenticated user.

6. The computing system of claim 5, wherein the one or more user interfaces comprise an interactive voice interface.

7. The computing system of claim 5, wherein the one or more user interfaces comprise an interactive graphical user interface.

8. The computing system of claim 5, wherein the authenticated user is at least one of a parent, guardian, or caregiver of the patient corresponding to the prescription resource.

9. One or more non-transitory computer readable media storing non-transitory computer executable instructions that, when executed by one or more processors, cause the one or more processors to:
  obtain an indication of a request to access a prescription resource, the request obtained via an electronic computing device associated with a user;
  obtain access permission information defining different respective permission sets of a plurality of persons to access prescription resources associated with the patient, the prescription resources including the requested prescription resource;
  identify an authentication action prerequisite to providing access to the requested prescription resource;
  identify a plurality of modes of communication modes usable to perform the authentication action;
  select, from the usable communication modes, a particular communication mode for performing the authentication action, the selecting of the particular communication mode comprising selecting a voice-based authentication, and the selecting being based upon at least one of (1) configuration information indicating compatibility of the electronic computing device to utilize each of the plurality of communication modes, or (2) contextual information indicating an environment in which the user is located;
  obtain voice data corresponding to the user, the voice data provided by the user via a microphone of the electronic computing device;
  compare the obtained voice data to reference voice data corresponding to each of the plurality of persons;
  based upon the comparison, identify the user as a particular one of the plurality of persons;
  based upon the identifying of the user, authenticate the identified user to access the requested prescription resource based upon the corresponding permission set for the identified user wherein the authentication based upon the comparison of the voice data is used in combination with one or more further authentication factors to authenticate the identified user to access the requested prescription resource; and
  provide one or more user interfaces to the electronic computing device to facilitate access to the requested prescription resource for the authenticated user.

10. The one or more non-transitory computer readable media of claim 9, wherein the one or more user interfaces comprise an interactive voice interface.

11. The one or more non-transitory computer readable media of claim 9, wherein the one or more user interfaces comprise an interactive graphical user interface.

12. The one or more non-transitory computer readable media of claim 9, wherein the authenticated user is at least one of a parent, guardian, or caregiver of the patient corresponding to the prescription resource.

* * * * *